United States Patent [19]

Redmore

[11] 4,154,948

[45] May 15, 1979

[54] PHOSPHONIUM COMPOUNDS

[75] Inventor: Derek Redmore, Ballwin, Mo.

[73] Assignee: Petrolite Corporation, St. Louis, Mo.

[21] Appl. No.: 888,596

[22] Filed: Mar. 20, 1978

Related U.S. Application Data

[60] Division of Ser. No. 776,816, Mar. 11, 1977, Pat. No. 4,117,236, which is a continuation of Ser. No. 300,289, Oct. 24, 1972, abandoned, which is a division of Ser. No. 30,956, Apr. 22, 1970, abandoned, which is a division of Ser. No. 581,771, Sep. 26, 1966, Pat. No. 3,531,514.

[51] Int. Cl.$^2$ ................................................ C07F 9/54
[52] U.S. Cl. ...................................... 560/8; 560/100; 560/102
[58] Field of Search ........................... 560/8, 100, 102

[56] References Cited

U.S. PATENT DOCUMENTS 3,736,349  5/1973  Gillham et al. ..................... 560/129

*Primary Examiner*—Jane S. Myers
*Attorney, Agent, or Firm*—Sidney B. Ring; Hyman F. Glass

[57] ABSTRACT

Phosphonium compounds of the formula

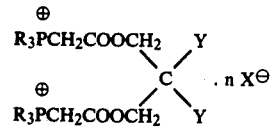

where y is $-CH_2OH$ or $-CH_2OOCCH_2PR_3$, n is an integer of 2–4, R is a substituted group, preferably hydrocarbon, such as alkyl, cycloalkyl, aryl, etc., and X is a negative ion. These compounds are used in inhibiting the corrosion of metals and particularly in preventing corrosion of metals, particularly iron, steel and ferrous alloys.

4 Claims, No Drawings

PHOSPHONIUM COMPOUNDS

This Application is a division of Application Ser. No. 776,816, filed Mar. 11, 1977, now U.S. Pat. No. 4,117,236, which in turn is a continuation of Application Ser. No. 300,289, filed Oct. 24, 1972, now abandoned, which in turn is a division of Application Ser. No. 30,956, filed Apr. 22, 1970, now abandoned, which in turn is a division of Application Ser. No. 581,771, filed on Sept. 26, 1966, now U.S. Pat. No. 3,531,514, granted Sept. 29, 1970.

This invention relates to phosphonium compounds and to uses therefore. It also relates to their use in inhibiting the corrosion of metals, and particularly in preventing corrosion of metals and particularly iron, steel, and ferrous alloys. The corrosion inhibitors contemplted herein find special utility in the prevention of corrosion of pipe or equipment which is in contact with a corrosive oil-containing medium, as, for example, in oil wells producing corrosive oil or oil-brine mixtures, in water floods, in refineries, and the like. These inhibitors may, however, be used in other systems or applications. They appear to possess properties which impart to metals resistance to attack by a variety of corrosive agents, such as brines, weak inorganic acids, organic acids, $CO_2$, $H_2S$, etc.

The compounds of this invention are quaternary phosphonium compounds. For convenience, these compounds may be described as compounds containing at least

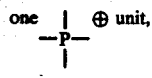

for example 1, 2, 3 or more phosphonium units, such as 10, 20, 30 or more in the case of polymeric structures. The groups attached to the phosphorus atoms may vary widely. The following are presented for purposes of illustration:

Allyl—methyl, ethyl, propyl, butyl, pentyl, and higher groups such as decyl, hexadecyl, etc.—straight chain, branched, etc.

Alkenyl—vinyl, allyl, etc., and other unsaturated groups having two or more carbon atoms, such as 18 or more carbons, which have one or more unsaturated groups such as linolyl, linolenyl, etc.

Alkinyl—propargyl, etc., and other acetylenic unsaturated groups having two or more carbon atoms such as 18 or more carbons having one or more acetylenic groups.

Aryl—phenyl, naphthyl, anthracyl, diphenyl, etc.; substituted aryl such as $R_n$-A where A is an aryl group and R is substituted group, the maximum value of n is determined by the available substitutable groups on A. It may be another Aryl group, alkyl, cycloalkyl, alkenyl, alkinyl, substituted derivatives thereof, etc.

Cycloalkyl—cyclopentyl, cyclohexyl, etc.

Cycloalkenyl—cyclohexenyl, etc.

Cycloalkinyl—cyclohexinyl, etc.

heterocyclic group—furfuryl, pyridinyl, thienyl, etc., i.e. cyclic compounds containing one or more non-carbon groups in the ring.

Any of the above groups may be substituted with non-carbon atoms—oxygen, nitrogen, sulfur, halogens, etc., which groups (1) may interrupt the main carbon chain such as $-\!(\!AO\!)\!_n$,

where A is alkylene, etc., such as ethylene, propylene, butylene, etc., for example $(-O-CH_2CH_2-)_n$

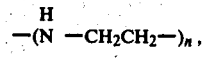

etc., or (2) be branched from the main carbon chain

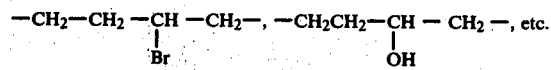

Two or more of the substituted groups attached to the phosphorus atoms may be the same, or each may be different. Furthermore, all groups need not be of the same type.

In addition, two valences of the phosphorus atoms may be joined to form a ring structure, for example,

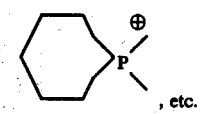

The type of phosphorus-containing ring may vary widely, may be substituted or may contain other than carbon atoms in the ring, for example,

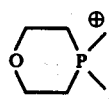

In addition, the phosphonium compound may contain more than one phosphonium group, for example,

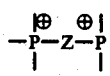

Where Z is a divalent group such as alkylene, alkylene ether, xylylene, etc., for example,

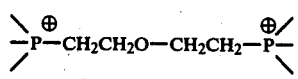

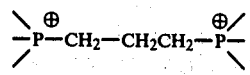

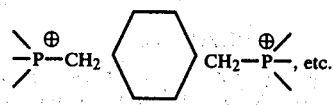

Three phosphonium groups for example,

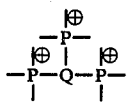

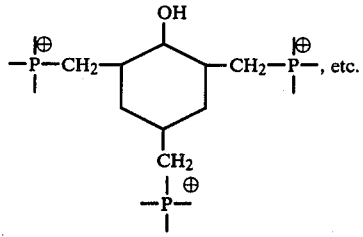

Polymeric phosphonium compounds such as with pendent groups, for example,

Polymer backbone

or in the backbone of the polymer itself

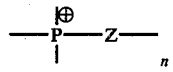

such as formed by reacting an alkylene dihalide with a phosphorus compound.

The negative moiety is generally halogen, e.g. chlorine, bromine, iodine, fluorine, but may be other negative groups such as sulfates, phosphate, sulfonate, or phosphonate, partial esters thereof, etc. Organic acids such as hydrocarbon sulfonic acids, acetic acid, oxalic acid, benzoic acid, maleic acid, oleic acid, perchloric acid, picric acid, etc.

The following examples are presented for purposes of illustration and not of limitation, to illustrate the wide variety of phosphonium compounds that can be prepared and employed herein. All temperatures are in ° C.

The following example illustrates diphosphonium compounds containing other than hydrocarbon groups in the molecule, in this case a diester diphosphonium compound of the general type:

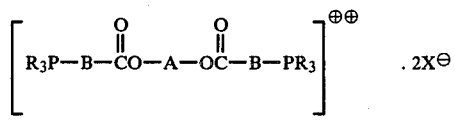

where A and B are hydrocarbon groups, such as for example alkylene, etc., and the R's which may be the same or different, are hydrocarbon groups such as alkyl, aryl, etc.

EXAMPLE 1

Ethylene glycol (0.125 mole) was heated under reflux with chloroacetic acid (0.25 mole) in xylene until esterification was completed by azeotropic removal of water (0.25 mole). After removal of xylene the resultant dihalide was dissolved in n butanol and reacted with tributyl phosphine (0.25 mole) by heating under reflux for ten hours in a nitrogen atmosphere. Evaporation of solvent yielded the diphosphonium salt which is readily soluble in methanol and easily dispersed in water. It has the following formula:

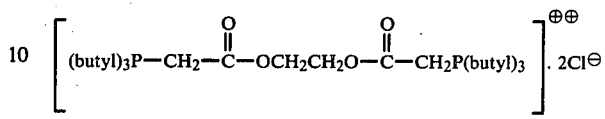

The following example illustrates phosphonium compounds containing hydroxy groups as well as ester groups, for example, of the general formula

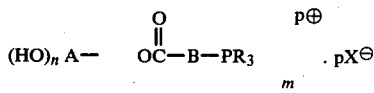

where A, B and R have the meaning as in Example 1 and n, m and p are integers.

EXAMPLE 2

Pentaerythritol (0.1 mole) was esterified with chloroacetic acid (0.2 mole) by the method used in Example 1. The resulting dihalide was heated for 16 hours under reflux with tributyl phosphine (0.2 mole) in a nitrogen atmosphere. The disphosphonium salt was obtained as a viscous gum, readily dispersible in water and soluble in methanol. It has the following formula:

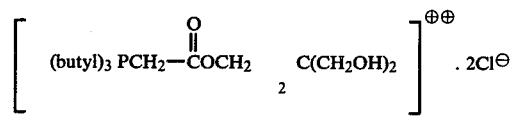

The following example illustrates a higher homologue of Example 1.

EXAMPLE 3

The dihalide from chloroacetic acid and ethylene glycol prepared as in Example 1 was reacted with trioctyl phosphine for ten hours under the quaternization conditions disclosed in Example 1. The disphosphonium salt obtained crystallized on cooling and was readily dispersed in water.

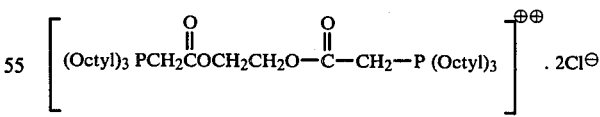

The following example illustrates a higher homologue of Example 2.

EXAMPLE 4

The dihalide of Example 2 prepared from pentaerythritol (0.125 mole) and chloroacetic acid (0.25 mole) was reacted with trioctyl phosphine (0.25 mole) in butanol in the manner of previous examples for ten hours. The resultant diphosphonium salt had similar properties to the product in Example 3.

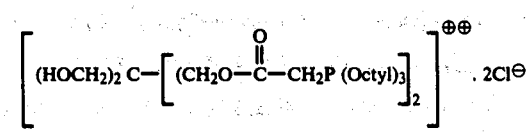

These compositions can be oxyalkylated with alkylene oxides such as ethylene oxide, propylene oxide, etc.

In addition, the composition of Example 4 may be completely esterified by employing a stoichiometric excess of chloroacetic acid to yield a compound of the formula.

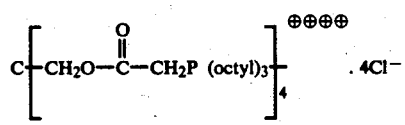

The following example illustrates a phosphonium compound which contains an aromatic and a nitrile group and a halide other than chlorine.

EXAMPLE 5

Phenyl phosphine was cyanoethylated by a standard procedure to yield dicyanoethyl phenyl phosphine. This tertiary phosphine (0.1 mole) was heated under reflux with propyl iodide (0.1 mole) in n-butanol for 24 hours in a nitrogen atmosphere to yield dicyanoethyl phenyl propyl phosphonium iodide. It has the following formula

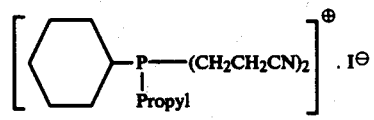

The following example illustrates the hydrolyzed product of Example 5.

EXAMPLE 6

Dicyanoethyl phenyl propyl phosphonium iodide (0.1 mole) was heated under reflux for three hours with 6 N hydrochloric acid (100 ml). Removal of the solvent yielded a dark gum whose infrared spectrum was characteristic of a carboxylic acid.

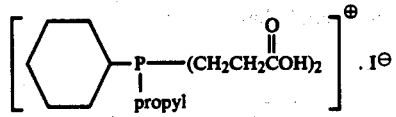

The following example illustrates the salt of Example 6.

EXAMPLE 7

The carboxylic phosphonium salt of Example 6 was neutralized with sodium hydroxide to give the corresponding sodium carboxylate.

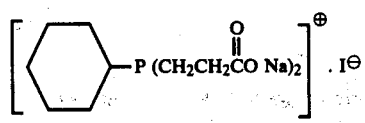

The following example illustrates a polymer having other than hydrocarbons in the chain and having pendent phosphonium groups.

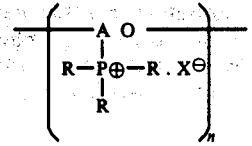

where A is for example alkylene, substituted alkylene, etc., ethylene, propylene, butylene, octylene, etc., and R is a hydrocarbon group—alkyl, cycloalkyl, phenyl, substituted groups thereof, etc.

These may be copolymerized by oxyalkylation, etc.

EXAMPLE 8

Polyepichlorohydrin (MW-1500) (0.5 equivalents) was heated under nitrogen with tributyl phosphine at 140°-150° for two hours during which time a homogeneous mixture was obtained. The product was readily water soluble and determination of ionic chlorine content indicated a 70% reaction.

It has the following formula

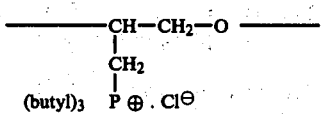

These compositions may be oxyalkylated with ethylene, propylene, etc., oxides to yield for example

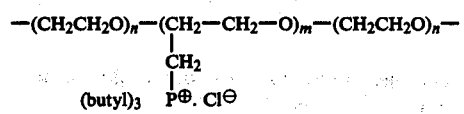

The following example illustrates a phosphonium compound having a carboxylic acid group.

EXAMPLE 9

To tributyl phosphine (0.2 moles) under nitrogen was added chloroacetic acid (0.2 moles) during 15 minutes. The reaction temperature reached 65°-70° during the addition. Upon completion of the addition, the reaction was continued by heating at 100° for two hours. The product was obtained as a colorless, viscous, water-soluble material.

It has the following formula

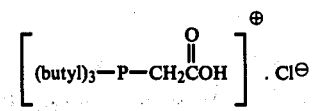

The following illustrates a homologue of Example 10.

EXAMPLE 10

The reaction of Example 9 was repeated using trioctyl phosphine yielding a product with very similar properties.

It has the following formula

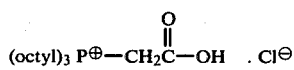

The following illustrates a polymer having a hydrocarbon backbone and pendent phosphonium groups which are linked to the hydrocarbon backbone through an ester group which has the following repetitive unit

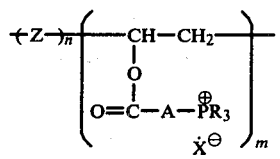

where A is a hydrocarbon group, such as alkylene, etc., and R is a hydrocarbon group such as alkyl, etc. and Z is a vinyl copolymer, for example, ethylene, propylene, styrene, butadiene, substituted derivatives thereof, etc.

EXAMPLE 11

An ethylene-vinyl alcohol copolymer (20% by weight vinyl alcohol) MW 5000 (27.6 g) was esterified with chloroacetic acid (12 g) by heating in xylene (200 ml) wth azeotropic removal of water. The resulting chloride was heated in butanol (100 ml) with tributyl phosphine (25.6 g) for 12 hours. The product was a polymeric quaternary phosphonium compound soluble in xylene.

It has the following repetitive formula

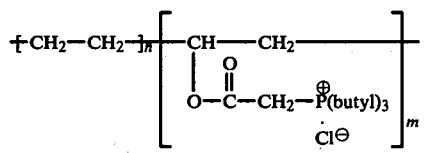

Other copolymers can also be employed such as a styrene, butadiene, etc.

The following examples illustrates a triaryl phosphonium compound

where Ⓐ is an aryl group, etc. A is an alkylene group, etc.,

EXAMPLE 12

Triphenyl phosphine (26 g; 0.1 mole) was heated under reflux with chloroacetic acid (9.5 g; 0.1 mole) in ethanol (150 ml) for four hours. Evaporation of the solvent yielded carboxymethyl triphenyl phosphonium chloride.

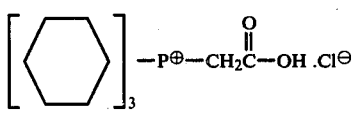

It should be noted that bromoacetic acid may be employed in the above examples in place of chloroacetic acid to yield bromo analogues having similar properties.

A wide variety of polyols can be used to prepare the compositions of this invention. For example, the Friedel-Craft condensates of hydrocarbons and carboxyhydrates such as described in U.S. Pat. No. 3,128,314 can also be treated with stoichiometric or less than stoichiometric amounts of haloacetic acid and then with phosphines, to yield polyphosphonium compounds. For example, 1-deoxyl-1, 1-di(o-xylyl)-D - glucitol (made from o-xylene and starch).

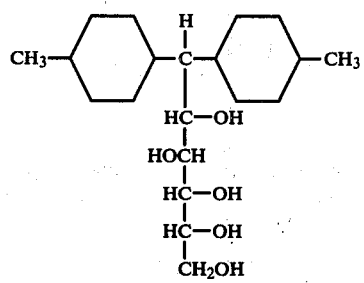

will yield

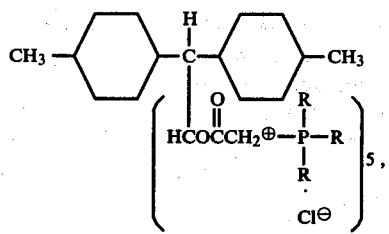

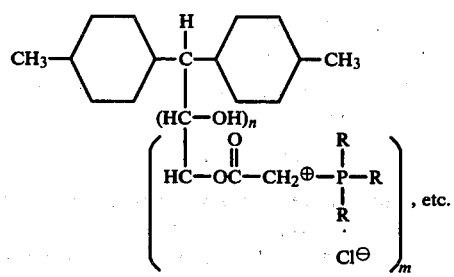

These compounds which contain hydroxy groups may also be oxyalkylated to yield

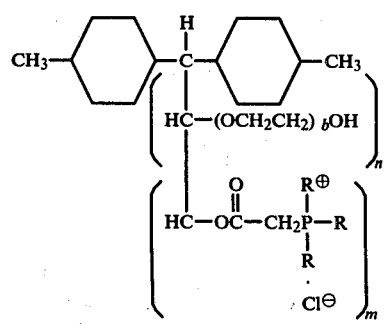

In addition, they can be reacted with epihalohydrin and then with phosphines, for example

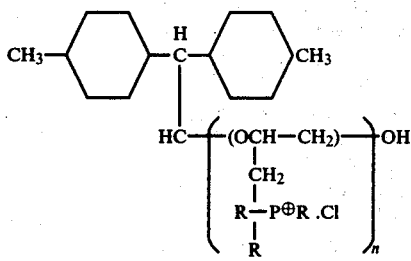

One preferred class of compounds of this invention are those which contain at least one ester group and at least one phosphonium group, with or without other functional groups. They may be monomeric, oligomeric, or polymeric.

In the most preferred embodiment, they are prepared by reacting an hydroxy containing compound with a halo-carboxylate to yield an halo ester which is then reacted with a phosphine to yield the esterphosphonium compound.

Another important class of polymeric phosphonium compounds is that derived from reacting epihalohydrin polymers with phosphines to yield polymers of the following type:

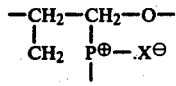

In addition, these may be copolymerized with alkylene oxides for example ethylene, propylene, butylene, octylene, styrene oxide, etc., in a block, random, etc. fashion.

USE AS CORROSION INHIBITORS

This phase of this invention relates to the use of phosphonium compounds in inhibiting the corrosion of metals, most particularly iron, steel and ferrous alloys. These compounds can be used in a wide variety of applications and systems where iron, steel and ferrous alloys are affected by corrosion. They may be employed for inhibiting corrosion in processes which require this protective or passivating coating as by dissolution in the medium which comes in contact with the metal. They can be used in preventing atmospheric corrosion, underwater corrosion, corrosion in steam and hot water systems, corrosion in chemical industries, underground corrosion, etc.

The corrosion inhibitors contemplated herein find special utility in the prevention of corrosion of pipe or equipment which is in contact with a corrosive oil-containing medium, as, for example, in oil wells producing corrosive oil or oil-brine mixtures, in refineries, and the like. These inhibitors may, however, be used in other systems or applications, They appear to possess properties which impart to metals resistance to attack by a variety of corrosive agents, such as brines, weak inorganic acids, organic acids, $CO_2$, $H_2S$, etc.

The method of carrying out this process is relatively simple in principle. The corrosion preventive reagent is dissolved in the liquid corrosive medium in small amounts and is thus kept in contact with the metal surface to be protected. Alternately, the corrosion inhibitor may be applied first to the metal surface, either as is, or as a solution in some carrier liquid or paste. Continuous application, as in the corrosive solution, is the preferred method, however.

The present process finds particular utility in the protection of metal equipment of oil and gas wells, especially those containing or producing an acidic constituent such as $H_2S$, $CO_2$, organic acids and the like. For the protection of such wells, the reagent, either undiluted or dissolved in a suitable solvent, is fed down the annulus of the well between the casing and the producing tubing where it becomes comingled with the fluid in the well and is pumped or flowed from the well with these fluids, thus contacting the inner wall of the casing, the outer and the inner wall of tubing, and the inner surface of all wellhead fittings, connections and flow lines handling the corrosive fluid.

Where the inhibitor composition is a liquid, it is conventionally fed into the well annulus by means of a motor driven chemical injector pump, or it may be dumped periodically (e.g., once every day or two) into the annulus by means of a so-called "bole weevil" device or similar arrangement. Where the inhibitor is a solid, it may be dropped into the well as a solid lump or stock, it may be blown in as a powder with gas, or it may be washed in with a small stream of the well fluids or other liquid. Where there is gas pressure on the casing, it is necessary, of course, to employ any of these treating methods through a pressure equalizing chamber equipped to allow introduction of reagent into the chamber, equilization of pressure between chamber and casing, and travel of reagent from chamber to well casing.

Occasionally, oil and gas wells are completed in such a manner that there is no opening between the annulus and the bottom of the tubing or pump. This results, for example, when the tubing is surrounded at some point by a packing held by the casing or earth formation below by the casing. In such wells the reagent may be introduced into the tubing through a pressure equalizing vessel, after stopping the flow of fluids. After being so treated the well should be left closed in for a period of time sufficient to permit the reagent to drop to the bottom of the well.

For injection into the well annulus, the corrosion inhibitor is usually employed as a solution in a suitable solvent. The selection of solvent will depend much upon the exact reagent being used and its solubility characteristics.

For treating wells with packed-off tubing, the use of solid "sticks" or plugs of inhibitor is especially convenient. These may be prepared by blending the inhibitor with a mineral wax, asphalt or resin in a proportion sufficient to give a moderately hard and high-melting solid which can be handled and fed into the well conveniently.

The protective action of the herein described reagents appears to be maintained for an appreciable time after treatment ceases, but eventually is lost unless another application is made.

For example, for the protection of gas wells and gas-condensate wells, the amount of corrosion inhibitor used might range between about ¼ to 3 lbs. more per million cubic feet of gas produced, depending upon the amounts and composition of corrosive agents in the gas and the amount of liquid hydrocarbon and water produced. However, in no case does the amount of inhibitor required appear to be stoichiometrically related to the amount of acids produced by a well, since protection is obtained with much less corrosion inhibitor than usually would be required for neutralization of the acids produced.

These compositions are particularly effective in the prevention of corrosion in systems containing a corrosive aqueous medium, and most particularly in systems containing brines.

These phosphonium compounds can also be used in the prevention of corrosion in the secondary recovery of petroleum by water flooding and in the disposal of waste water and brine from oil and gas wells. Still more particularly, they can be used in a process of preventing corrosion in water flooding and in the disposal of waste water and brine from oil and gas wells which is characterized by injecting into an underground formation or aqueous solution containing minor amounts of the compositions of this invention, in sufficient amounts to prevent the corrosion of metals employed in such operation.

When an oil well ceases to flow by the natural pressure in the formation and/or substantial quantities of oil can no longer be obtained by the usual pumping methods, various processes are sometimes used for the treatment of the oil-bearing formation in order to increase the flow of oil. These processes are usually described as secondary recovery processes. One such process which is used quite frequently is the water flooding process wherein water is pumped under pressure into what is called an "injection well" and oil, along with quantities of water, that have been displaced from the formation, are pumped out of an adjacent well usually referred to as a "producing well". The oil which is pumped from the producing well is then separated from the water that has been pumped from the producing well and the water is pumped to a storage reservoir from which it can again be pumped into the injection well. Supplementary water from other sources may also be used in conjunction with the produced water. When the storage reservoir is open to the atmosphere and the oil is subject to aertion this type of water flooding system is referred to herein as an "open water flooding system". If the water is recirculated in a closed system without substantial aeration, the secondary recovery method is referred to herein as a "closed water flooding system".

Because of the corrosive nature of oil field brines, to economically produce oil by water flooding, it is necessary to prevent or reduce corrosion since corrosion increases the cost thereof by making it necessary to repair and replace such equipment at frequent intervals. These compositions can be employed in preventing corrosion in systems containing a corrosive aqueous media, and most particularly in systems containing brine, which is characterized by employing the phosphonium compounds described herein. For example, they can be employed in an improved process of protecting from corrosion metallic equipment employed in secondary oil recovery by water flooding such as injection wells, transmission lines, filters, meters, storage tanks, and other metallic implements employed therein and particularly those containing iron, steel, and ferrous alloys, such process being characterized by employing in water flood operation an aqueous solution of the compositions of this invention.

In many oil fields large volumes of water are produced and must be disposed of where water flooding operations are not in use or where water flooding operations cannot handle the amount of produced water. Most States have laws restricting pollution of streams and land with produced waters, and oil producers must then find some method of disposing of the waste produced salt water. In many instances therefore, the salt water is dispersed by injecting the water into permeable low pressure strata below the fresh water level. The formation into which the water is injected is not the oil producing formation and this type of disposal is defined as salt water disposal or waste water disposal. The problems of corrosion of equipment are analogous to those encountered in the secondary recovery operation by flooding. The compositions of this invention can also be used in such water disposal wells thus providing a simple and economical method of solving the corrosion problems encountered in disposing of unwanted water.

Water flood and waste disposal operations are too well known to require further elaboration. In essence, the flooding operation is effected in the conventional manner except that the flooding medium contains a minor amount of these compounds, sufficient to prevent corrosion.

While the flooding medium employed in accordance with the present invention contains water or oil field brine and the compounds of this invention, the medium may also contain other materials. For example, the flooding medium may also contain other agents such as surface active agents or detergents which aid in wetting throughout the system and also promote the desorption of residual oil from the formation, sequestering agents which prevent the deposition of calcium and/or magnesium compounds in the interstices of the formation, bacteriocides which prevent the formation from becoming plugged through bacterial growth, tracers, etc. Similarly, they may be employed in conjunction with any of the operating techniques commonly employed in water flooding peripheral flooding, etc. and in conjunction with other secondary recovery methods.

The concentration of the corrosion inhibitors of this invention will vary widely depending on the particular compound, the particular system, etc. Concentrations of at least about 0.25 ppm, such as about 0.75 to 7,500 ppm for example about 1 to 5,000 ppm, advantageously about 10 to 1,000 ppm, but preferable about 15-250 ppm may be employed. Larger amounts can also be employed such as 1.5-5.0% although there is generally no commercial advantage in so doing.

For example, since the success of a water flooding operation manifestly depends upon its total cost being less than the value of the additional oil recovered from the oil reservoir, it is quite important to use as little as possible of these compounds consistent with optimum corrosion inhibition.

Since these compounds are themselves inexpensive and are used in low concentrations, they enhance the success of a flood operation by lowering the cost thereof.

By varying the constituents of the composition, the compounds of this invention can be made more oil or more water soluble, depending on whether the composition is to be employed in oil or water systems.

Although the manner of practicing the present invention is clear from the foregoing description, the following non-limiting specific examples are included for purposes of illustration.

Examples

These tests were run under conditions so set up as to simulate those found in an actual producing well. The test procedure involved the measurement of the corrosive action of fluids inhibited by the composition herein described upon sandblasted SAE 1020 steel coupons measuring ¼ inch in diameter and being 4 inches long when compared to test coupons containing no inhibitor and commercial inhibitors.

Clean pint bottles were half-filled (almost 200 ml) with sea-water (i.e., tap water containing 3% by weight of the salts, magnesium chloride, calcium chloride, sodium sulfate and sodium chloride) which had been saturated with hydrogen sulfide. Those requiring inhibitor were charged with the same by pipetting calculated amounts contained in suitable solvents (water, isopropyl alcohol, mineral spirits) to give the required parts per million of inhibitor. Uninhibited blanks were run in conjunction with inhibited solutions. The bottles were now filled (total volume now about 400 ml.) leaving a small air space to allow for expansion. The weighed coupons attached to sealing caps were screwed onto the bottles and they were placed on a rotating wheel for seven days at 115° F. The coupons were then removed, cleaned electrolytically in 5% sulfuric acid (using the coupons as a cathode) and washed successively with dilute sodium hydroxide, twice with water, once with acetone and finally dried.

When the inhibitor was oil-soluble as contrasted to water-soluble, a two-phase system was used instead of the "allbrine system" and this simply consisted of using hydrogen sulfide saturated mineral spirits to replace 25% by volume of the brine.

The changes in the weights of the coupons during the corrosion test were taken as a measurement of the effectiveness of the inhibitor compositions. Protective percentage was calculated for each test coupon taken from the inhibited fluids in accordance with the following formula:

$$\frac{W_1 - W_2}{W_1} \times 100 = \text{percent protection}$$

in which $W_1$ is the less in weight of the coupon taken from uninhibited fluids and $W_2$ is the loss in weight of coupons which were subjected to inhibited fluids.

The results obtained are presented in the following Table I.

All of the compositions prepared in the above examples are advantageously employed as corrosion inhibitors. The following examples are presented as exemplary.

TABLE I

| PERCENT PROTECTION AT PARTS PER MILLION (ppm) IN BRINE —H₂S SYSTEMS | | | |
|---|---|---|---|
| | 4 ppm | 8 ppm | 15 ppm |
| Example 1 | 60 | 48 | 55 |
| Example 2 | 70 | 50 | 84 |
| Example 3 | 69 | 84 | 67 |
| Example 4 | 64 | 60 | 57 |
| Example 5 | 43 | 65 | 58 |
| Example 7 | 88 | 75 | 83 |
| Example 8 | 41 | 78 | 81 |
| Commercial Inhibitor | 22 | 53 | 55 |

TABLE II

| PERCENT PROTECTION AT ppm IN OIL BRINE (25/75 —CO₂ SYSTEMS | | | | |
|---|---|---|---|---|
| Example 3 | 100 | 100 | 100 | 100 |
| Example 4 | 35 | 100 | 100 | 100 |
| Commercial Inhibitor | 50 | 53 | 82 | 92 |

These phosphoniums can also be employed in conjunction with other corrosion inhibitors, for example, of the film-forming type. Non-limiting examples include the acylated polyamines such as described in U.S. Pat. Re. Nos. 23, 227, 2,466,517, 2,468,163, 2,598,213 and 2,640,029. These acylated polyamines may be described as amides, imidazolines, tetrahydropyrimidines, etc.

As is quite evident, many phosphonium compounds will be constantly developed which could be useful in this invention. It is, therefore, not only impossible to attempt a comprehensive catalogue of such compositions, but to attempt to describe the invention in its broader aspects in terms of specific chemical names used would be too voluminous nd unnecessary since one skilled in the art could by following the description of the invention herein select a useful phosphonium compound. This phase of the invention lies in the use of phosphonium compounds as corrosion inhibitors and their individual compositions are important only in the sense that their properties can affect this function. To precisely define such specific useful phosphonium compound in light of the present disclosure would merely call for chemical knowledge within the skill of the art in a manner analogous to a mechanical engineer who prescribes in the construction of a machine the proper materials and the proper dimensions thereof. From the description in this specification and with the knowledge of a chemist, one will know or deduce with confidence the applicability of specific phosphonium compounds suitable for this invention by applying them in the processes set forth herein. In analogy to the case of a machine, wherein the use of certain materials of construction or dimensions of parts would lead to no practical useful results, various materials will be rejected as inapplicable where others would be operative. One can obviously assume that no one will wish to use a useless phosphonium compound nor will be misled because it is possible to misapply the teachings of the present disclosure to do so. Thus, any phosphonium compound that can perform the function stated herein can be employed.

OTHER USES

In addition to the uses described above, these compositions and/or derivatives thereof, can be used as follows:

(1) as demulsifiers for O/W and W/O emulsions
(2) as biocides i.e. bactericides, algicides, etc.
(3) as additives to various petroleum fuels including gasoline, diesel fuel, jet fuels, etc.
(4) as gasoline anti-icers and anti-stallers
(5) as additives for sludging oil and cutting oils
(6) as agents for the textile industry such as mercerizing assistants, wetting agents, rewetting agents, penetrating agents, dispersing agents softening agents, dyeing assistants, etc.
(7) as anti-static agents for textile, plastics, etc.
(8) as lube oil additives
((9) as emulsifiers for insecticidal and agricultural compositions
(10) as floculants, particularly as flocaids

Having thus described my invention what I claim as new and desire to obtain by Letters Patent is

1. A phosphonium acetic acid ester of pentaerythritol of the formula

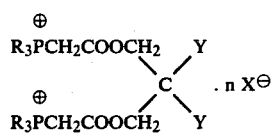

where

Y is —CH₂OH or

—CH₂OOCCH₂PR₃⊕, n is an integer of 2–4,

R is an aryl radical selected from the group consisting of
  phenyl, naphthyl, anthracyl and diphenyl radicals, and X is halogen, sulfate, phosphate, sulfonate, phosphonate, acetate, oxalate, benzoate, maleate, oleate, perchlorate or picrate.

2. The ester of claim 1 where each Y is —CH₂OH.
3. The ester of claim 1 where X is a halogen.
4. The ester of claim 1 where R is phenyl.

* * * * *